(12) United States Patent
Kubota et al.

(10) Patent No.: US 9,012,499 B2
(45) Date of Patent: Apr. 21, 2015

(54) PHARMACEUTICAL COMPOSITION COMPRISING OSELTAMIVIR PHOSPHATE

(75) Inventors: Ryuji Kubota, Tokyo (JP); Tomoaki Ohta, Tokyo (JP); Tomoaki Hirayama, Tokyo (JP); Hiroyuki Maeda, Tokyo (JP); Christian Volland, Loerrach (DE); Hans-Guenter Kaestle, Buggingen (DE)

(73) Assignees: Chugai Seiyaku Kabushiki Kaisha, Tokyo (JP); F. Hoffman-la Roche AG, Basel (CH)

( * ) Notice: Subject to any disclaimer, the term of this patent is extended or adjusted under 35 U.S.C. 154(b) by 0 days.

(21) Appl. No.: 12/161,336

(22) PCT Filed: Feb. 20, 2007

(86) PCT No.: PCT/JP2007/053081
§ 371 (c)(1),
(2), (4) Date: Jul. 17, 2008

(87) PCT Pub. No.: WO2007/097325
PCT Pub. Date: Aug. 30, 2007

(65) Prior Publication Data
US 2010/0222427 A1    Sep. 2, 2010

(30) Foreign Application Priority Data

Feb. 20, 2006   (JP) ................................. 2006-042178

(51) Int. Cl.
*A61K 31/215* (2006.01)
*A61K 9/14* (2006.01)
*A61K 9/16* (2006.01)

(52) U.S. Cl.
CPC ... *A61K 9/14* (2013.01); *A61K 9/16* (2013.01); *A61K 9/1623* (2013.01); *A61K 31/215* (2013.01)

(58) Field of Classification Search
None
See application file for complete search history.

(56) References Cited

U.S. PATENT DOCUMENTS

| | | | | |
|---|---|---|---|---|
| 4,292,451 | A * | 9/1981 | deBerardinis et al. | 568/863 |
| 5,952,375 | A | 9/1999 | Bischofberger et al. | |
| 6,534,087 | B2 * | 3/2003 | Busson et al. | 424/464 |
| 2003/0044457 | A1 | 3/2003 | Faour et al. | |
| 2004/0062801 | A1 * | 4/2004 | Faour et al. | 424/468 |
| 2004/0202714 | A1 * | 10/2004 | Nomura et al. | 424/464 |
| 2009/0176877 | A1 * | 7/2009 | Li et al. | 514/529 |
| 2010/0092564 | A1 * | 4/2010 | Park et al. | 424/489 |

FOREIGN PATENT DOCUMENTS

| | | |
|---|---|---|
| EP | 2005945 A2 | 12/2008 |
| JP | 1-268627 A | 10/1989 |
| JP | 827033 | 1/1996 |
| JP | 1036291 | 2/1998 |
| JP | 11035486 | 2/1999 |
| JP | 11-130663 A | 5/1999 |
| JP | 11310539 | 11/1999 |
| JP | 2000505801 | 5/2000 |
| JP | 2004-81221 A | 3/2004 |
| JP | 63156719 | 10/2008 |
| WO | 9728788 | 8/1997 |
| WO | 9738960 | 10/1997 |
| WO | 9807685 | 2/1998 |
| WO | 9943306 | 9/1999 |
| WO | 0200201 A2 | 1/2002 |
| WO | 2007043538 A1 | 4/2007 |

OTHER PUBLICATIONS

Dubost et al., "Characterization of a Solid State Reaction Product from a Lyophilized Formulation of a Cyclic Heptapeptide: A Novel Example of an Excipient-Induced Oxidation," Pharm. Res. 13, 1811-14 (1996).*
"Drug-Excipient Interactions" by Crowley et al., Pharma. Tech. Europe (Mar. 2001).*
"Organic Chemistry," 3rd Ed., by McMurry, Brooks/Cole Publishing Co. (California), pp. 723-724 (1992).*
"March's Advanced Organic Chemistry," by Smith et al., John Wiley & Sons, Inc. (New York), p. 1186 (2001).*
"Comparison of Reactivity of Amphetamine, Methamphetamine, and Dimethylamphetamine with Lactose and Related Compounds" by Duvall et al., J. Pharm. Sci. 54, 607-11 (1965).*
Chemical Structures of Glucose and Mannose (retrieved from STN on Dec. 16, 2014).*
"Oseltamivir Phosphate", Drug of the Future, 24, 11, 1999, 1189-1202.
Hayden et al., Use of the selective oral neuraminidase inhibitor oseltamivir to prevent influenza, The New England Journal of Medicine, 341(18):1336-1343 (1999).
McClellan et al., Oseltamivir: A review of its use in influenza, Drugs, 61(2):263-283 (2001).
Package insert of TAMIFLU® dry syrup 3% published in 2005 (from Office Action in corresponding Japanese Patent Application No. 2008-501722).
European Search Report in corresponding European Appl. No. 07714585.5 dated Sep. 17, 2012.
Food Chemicals Codex, 5th edition, pp. 153 and 278 (Jan. 1, 2004).

* cited by examiner

*Primary Examiner* — Theodore R West
(74) *Attorney, Agent, or Firm* — Browdy and Neimark, PLLC

(57) ABSTRACT

The present invention provides a pharmaceutical composition comprising: one or more excipients selected from sugars and sugar alcohols in which equilibrium water content is 1% by weight or less at 25° C. and at 70% relative humidity; and oseltamivir phosphate, wherein an amount of each of glucose and mannose contained in the sugars and sugar alcohols as impurities is 0.01% by weight or less.

8 Claims, No Drawings

PHARMACEUTICAL COMPOSITION COMPRISING OSELTAMIVIR PHOSPHATE

TECHNICAL FIELD

The present invention relates to a pharmaceutical composition containing oseltamivir phosphate, in particular, to a pharmaceutical composition containing oseltamivir phosphate that is superior in long-term preservation stability, as well as a solid formulation containing oseltamivir phosphate.

BACKGROUND ART

Oseltamivir phosphate [compound name: (−)-ethyl (3R, 4R,5S)-4-acetamido-5-amino-3-(1-ethylpropoxy)-cyclohex-1-ene-1-carboxylate monophosphate] has a potent inhibitory activity against neuraminidase of influenza virus (Patent Document 1), and has been used as an active ingredient of Tamiflu (Registered Trade Mark) that is a preventive or therapeutic agent of influenza.

Oseltamivir phosphate has been used widely as a capsule formulation, and recently, formulated as dry syrup especially for convenience of pediatric use. In general, powder or granules including divided fine granules (hereinafter referred to as "granules and the like") has to be stored under predetermined conditions once opened until used up. Compared to tablets and capsules that are packaged in unit dosage form, granules and the like are desired to have higher stability against light, humidity, temperature and the like in the storage environment. In particular, it is desired to provide granules and the like in which coloring, coagulation and aggregation are prevented. However, there has been no report on the preservation stability of the oseltamivir phosphate formulation of granules and the like. Also, there has been no report on the influence of additives on oseltamivir phosphate.

Patent Document 1: International Publication WO1998/007685 pamphlet

DISCLOSURE OF THE INVENTION

Problems to be Solved by the Invention

The object of the present invention is to provide a pharmaceutical composition containing oseltamivir phosphate that has an improved preservation stability, in particular, the preservation stability against humidity, temperature and the like in the storage environment, and further in which coloring during the storage is prevented.

Measures to Solve the Problems

The present inventors have worked hard to solve such problems and succeeded to complete the present invention by finding the improved preservation stability in a formulation of oseltamivir phosphate which contains a specific excipient.

That is, in one aspect of the present invention, there is provided a pharmaceutical composition comprising:

one or more excipients selected from sugars and sugar alcohols in which equilibrium water content is 1% by weight or less at 25° C. and at 70% relative humidity; and oseltamivir phosphate, wherein an amount of each of glucose and mannose contained in the sugars and sugar alcohols as impurities is 0.01% by weight or less.

In another aspect of the present invention, there is provided a pharmaceutical composition defied herein as the present invention, containing the excipients and oseltamivir phosphate, wherein the excipient is one or a mixture of two or more of sugars or sugar alcohols selected from erythritol, D-mannitol and sucrose.

Here, the pharmaceutical composition according to the present invention may be used for prevention or treatment of influenza virus infection and conditions associated with the infection selected from bronchitis, pneumonia, generalized pain and fever.

Further, the pharmaceutical composition according to the present invention may contain optional components, such as water-soluble polymers, high-intensity sweeteners, anti-caking agents and the like. Here, the water-soluble polymers that may be used in the present invention may be selected preferably from povidone, methylcellulose, carmellose sodium (synonymous with "sodium carboxymethylcellulose"; hereinafter referred to as carmellose sodium) and macrogol 6000. Still further, the high-intensity sweeteners that may be used in the present invention may be selected, for example, preferably from dipotassium glycyrrhizate, stevia extracts, acesulfame potassium, and saccharin sodium. Also, the anti-caking agents that may be used in the present invention are not particularly limited, but for example, may be light anhydrous silicic acid or cornstarch, and preferably light anhydrous silicic acid may be used.

In still another aspect of the present invention, there is provided a pharmaceutical composition defied herein as the present invention with the dosage form of granules and the like.

In still another aspect of the present invention, there is provided a method for prevention or treatment of influenza virus infection and conditions associated with the infection selected from bronchitis, pneumonia, generalized pain and fever, comprising administration of a pharmaceutical composition which comprises:

one or more pharmaceutically acceptable excipients selected from sugars and sugar alcohols in which equilibrium water content is 1% by weight or less at 25° C. and at 70% relative humidity; and an effective amount of oseltamivir phosphate, wherein an amount of each of glucose and mannose contained in the sugars and sugar alcohols as impurities is 0.01% by weight or less.

EMBODIMENTS OF THE INVENTION

The present invention will be illustrated more particularly hereinafter.

Oseltamivir phosphate used in the present invention may be synthesized, for example, by the method disclosed in International Publication WO1998/007685, WO1996/026933 and the like. Oseltamivir phosphate may be used, for example, for prevention or treatment of influenza virus infection and conditions associated with the infection selected from bronchitis, pneumonia, generalized pain and fever, and particularly preferably used for treatment or prevention of influenza virus infection type A or type B.

Since oseltamivir phosphate has a bitter taste, it is preferable to take measures for reducing the bitterness at the time of formulation. Normally, the bitterness may be masked by filling in a capsule and the like, but syrups and the like for pediatric use, which are administered in solution form, require some measures for reducing bitterness in the formulation. Thus, from the viewpoint of reducing the bitterness of oseltamivir phosphate, it is preferable that the composition ratio of oseltamivir phosphate in the unit dosage formulation is the lower. On the other hand, the unit dosage formulation having a smaller total amount may be administered with a smaller burden for patients and the active ingredient may be administered more efficiently. From this viewpoint, it is preferable that the composition ratio of the active ingredient in the unit dosage formulation is the higher. Further, in general it is considered that the higher the composition ratio of the active ingredient in the formulation, the more it is stable. From the above viewpoint, the composition ratio of oseltamivir phosphate in the formulation may be determined appropriately by a person skilled in the art, and it may be, for example, 1 to 10% by weight, preferably 1 to 7% by weight, and more preferably 3 to 5% by weight in the formulation.

Sugars and sugar alcohols (excipients) used in the pharmaceutical composition of the present invention have a characteristic that their equilibrium water content is 1% by weight or less at 25° C. and at 70% relative humidity. That is, the equilibrium water content may be obtained by leaving the samples (sugars or sugar alcohols) in the air that has been held in the predetermined condition of 25° C. and 70% relative humidity for a long time, and then by measuring when the water content in the samples become constant.

Specific examples of sugars and sugar alcohols that may be used in the present invention include erythritol, D-mannitol and sucrose (synonymous with "white sugar" or "cane sugar"; hereinafter referred to as sucrose) and the like, and the preferable sugars and sugar alcohols include erythritol, D-mannitol and sucrose (white sugar), and especially, erythritol is preferably used.

Further, sugars and sugar alcohols used in the pharmaceutical composition of the present invention are characterized in that they contain 0.01% by weight or less of each of glucose and mannose as impurities. The contents of glucose and mannose in these sugars and sugar alcohols may be measured by methods publicly known in the art regarding pharmaceutical formulation (for example, HPLC method). Sugars and sugar alcohols described above may be obtained by purifying sugars and sugar alcohols, which are produced by general procedure, by a column separation method or recrystallization method, or by both methods.

One or more water-soluble polymers used in the pharmaceutical composition of the present invention may be used for convenience for preparation of the formulation as necessary by methods publicly known in the technical field of pharmaceutical formulation. The water-soluble polymers that may be used in the present invention are not limited in particular, but specific examples thereof include povidone, pullulan, hydroxypropylcellulose, methylcellulose, hydroxypropylmethylcellulose, carmellose sodium, carmellose potassium, macrogol 6000, gelatin and gelatinized starch. Preferable examples include povidone, methylcellulose, carmellose sodium and macrogol 6000, and more preferable examples are povidone, methylcellulose and carmellose sodium. In the present invention, the water-soluble polymers may be used particularly as a binder for improving the production suitability of the formulation when the preparation is carried out by the wet granulation method. For example, the wet granulation step may be carried out after mixing this water-soluble polymer powder with other solid materials in the formulation, or a solution of all or a part of this water-soluble polymer dissolved in water may be added at the granulation step.

One or more the high-intensity sweetener used in the pharmaceutical composition of the present invention may include, as necessary, high-intensity sweeteners publicly known in the technical field of pharmaceutical formulation. The high-intensity sweeteners in the present invention mean the sweeteners which are sweeter than sucrose. The examples of the particular high-intensity sweeteners that are considered to be used in the present invention include saccharin sodium, stevia extracts, glycyrrhizinic acid, a salt of glycyrrhizinic acid (including dipotassium glycyrrhizate and the like), thaumatin, sucralose, acesulfame potassium and saccharin, preferably dipotassium glycyrrhizate, stevia extracts, acesulfame potassium and saccharin sodium, and particularly preferable to use are saccharin sodium, dipotassium glycyrrhizate and acesulfame potassium. In the present invention the high-intensity sweeteners may be used for masking the bitter taste of oseltamivir phosphate in the formulation of dry syrup and the like. For example, the wet granulation step may be carried out after mixing the powder of this high-intensity sweetener with other solid materials in the formulation, or a solution of all or a part of this high-intensity sweetener dissolved in water may be added at the granulation step.

One or more the anti-caking agents used in the pharmaceutical composition of the present invention may be used to prevent aggregation of the formulation in the storage environment, as necessary, by the publicly known method in the technical field of pharmaceutical formulation. The anti-caking agents that may be used in the present invention are not particularly limited, but specific examples thereof include hydrated silicon dioxide, light anhydrous silicic acid, crystalline cellulose, titanium oxide, cornstarch and low-substituted hydroxypropylcellulose, and preferably light anhydrous silicic acid and cornstarch, and more preferably light anhydrous silicic acid may be used. This anti-caking agent may be used, for example, by adding the powder of the agent to granules and by mixing.

Sugars and sugar alcohols described above, which are used as excipients in the present invention, also function as extenders for preparing the formulation, and therefore from that viewpoint, the composition ratio of the sugar and sugar alcohol in the formulation may be determined appropriately by a person skilled in the art. The composition ratio of sugar and sugar alcohol in the pharmaceutical composition of the present invention (the total amount of sugars and sugar alcohols, if a plurality of sugars and sugar alcohols are used) is, for example, 75 to 98% by weight, preferably 80 to 92% by weight.

The pharmaceutical composition of the present invention may further contain optional components such as a water-soluble polymer, a high-intensity sweetener and an anti-caking agent.

The amount of the water-soluble polymer to be added (the total amount, if a plurality of water-soluble polymers are used) is not limited but, for example, 0.5 to 20% by weight, preferably 1 to 10% by weight range may be added.

The amount of the high-intensity sweetener to be added (the total amount, if a plurality of high-intensity sweeteners are used) is not limited but, for example, 0.01 to 5% by weight, preferably 0.05 to 2% by weight range may be added.

The amount of the anti-caking agent to be added (the total amount, if a plurality of anti-caking agents are used) is not limited but, for example, 0.01 to 5% by weight, preferably 0.05 to 2% by weight range may be added.

The pharmaceutical composition of the present invention may also contain further additional optional components. The optional components to be added are not limited as long as they are the components that are normally used in pharmaceutical formulations. The particular examples include flavoring agents, suspending agents, thickening agents, fluidizing agents, disintegrating agents, dispersing agents, flavors and the like. Cornstarch, partially pregelatinized starch or the like may be suitably used as a disintegrating agent or a dispersing agent. In that case, they may be used in amount of 10% by weight or less, preferably 3 to 5% by weight. Conveniently, flavors may be used as a premixed flavor mixed with a publicly known carrier that is used in pharmaceutical compositions. It may be used in the amount of 2% by weight or less.

In the present invention, the pharmaceutical composition of the present invention may be prepared by combining oseltamivir phosphate and aforementioned sugars or sugar alcohols appropriately with each component described above.

The form of the pharmaceutical composition of the present invention is not limited, and is preferably an oral solid formulation, for example, tablets, capsules, powder, granules, fine granules and dry syrups, and especially preferable is powder, granules, fine granules, and dry syrups. Here, dry syrups mean solid formulations that form syrups by adding water and the like to be dissolved or suspended before administration. Further, the powder, granules and fine granules referred to in the present specification are in accordance with the standard described in the Pharmacopeia of Japan. For example, the granules are prepared by making the pharmaceutical composition in granular form, and all of which pass through a No. 10 sieve (1700 μm), 5% of total amount or less are retained by a No. 12 sieve (1400 μm) and 15% of total amount or less passes by a No. 42 sieve (355 μm). The powder is prepared by making the pharmaceutical composition in powder form, and all of which passes through a No. 18 sieve (850 μm), and 5% of total amount or less are retained by a No. 30 sieve (500 μm). The powder in which 10% of the whole or less passes through a No. 200 sieve (75 μm) can be called as fine granules.

The present invention relates to a pharmaceutical composition comprising oseltamivir phosphate and sugars or sugar alcohols (excipient), preferably comprising oseltamivir phosphate, sugars or sugar alcohols (excipient) and high-intensity sweeteners, and more preferably comprising oseltamivir phosphate, sugars or sugar alcohols (excipient), high-intensity sweeteners and water-soluble polymers, and the most preferable combination is oseltamivir phosphate, sugars or sugar alcohols, high-intensity sweeteners, water-soluble polymers and anti-caking agent.

The composition ratios in the most preferable pharmaceutical composition are
Preferably:
  a) oseltamivir phosphate: 1 to 10% by weight;
  b) aforementioned excipients: 75 to 98%;
  c) water-soluble polymers: 0.5 to 20% by weight;
  d) high-intensity sweeteners: 0.01 to 5% by weight;
  e) anti-caking agent: 0.01 to 5% by weight
More preferably:
  a) oseltamivir phosphate: 1 to 7% by weight;
  b) aforementioned excipients: 80 to 92%;
  c) water-soluble polymers: 1 to 10% by weight;
  d) high-intensity sweeteners: 0.05 to 2% by weight;
  e) anti-caking agent: 0.05 to 2% by weight
Even more preferably:
  a) oseltamivir phosphate: 3 to 5% by weight;
  b) aforementioned excipients: 83 to 90%;
  c) water-soluble polymers: 2 to 5% by weight;
  d) high-intensity sweeteners: 0.05 to 1% by weight;
  e) anti-caking agent: 0.05 to 1% by weight,
and this pharmaceutical composition may contain optional components as necessary.

EXAMPLES

Following is a detailed description of the preferred examples of the present invention, but the present invention is not limited to these examples. Unless otherwise specified, the values of percentage in the examples are expressed by % by weight.

(1) Method for Measuring Equilibrium Water Content
  Equilibrium water content (25° C., relative humidity 70%) of sugars and sugar alcohols can be measured by the method using a DVS-1 (Surface Measurement Systems Ltd.). The condition for measurement is as follows.
  Quantity of samples: 50 to 100 mg (intending to scale 75 mg)
  Measurement temperature: 25±1° C.
  Setting range of relative humidity: 0 to 100% RH
  Measurement step of relative humidity: up to 10%
  Hold time: If change of the weight is less than 0.02%, the measurement enters next step, but the change is not stable, the step lasts up to 120 min.

(2) Method for Measuring Impurities (Glucose, Mannose).
  Glucose and mannose present in sugars and sugar alcohols as impurities were separated by ion chromatography and determined the quantity thereof by electrochemical detection. The condition for measurement is as follows.
  Measurement Conditions for HPLC
  Detector: electrochemical detector
  Column: CarboPac PA-1
  Column temperature: room temperature
  Mobile phase A: water; mobile phase B: 10 mM sodium hydroxide aqueous solution; mobile phase C: 200 mM sodium hydroxide aqueous solution
  Gradient: set as shown in Table 1. The composition ratio of the mobile phase is described by volume %

TABLE 1

| The setting of gradient (solvent composition) | | | | | | |
|---|---|---|---|---|---|---|
| | Time (min) | | | | | |
| | 0 | 30 | 50 | 50.01 | 60 | 60.01 | 75 |
| Mobile phase A (%) | 90 | 0 | 0 | 0 | 0 | 90 | 90 |
| Mobile phase B (%) | 10 | 100 | 100 | 0 | 0 | 10 | 10 |
| Mobile phase C (%) | 0 | 0 | 0 | 100 | 100 | 0 | 0 |

Analysis time: 50 min
Injection interval: 75 min
Flow rate: 1 mL/min
Amount of injected sample: 25 μL
Post column: Immediately before the detector, 300 mM sodium hydroxide solution was delivered at a flow rate of about 2 mL/min.

To obtain standard curves, 0.5, 5, 25, 50 μg/mL aqueous solutions of D-glucose and D-mannose were prepared as standard solutions. The concentrations of the standard solutions were equivalent to 0.001, 0.01, 0.05 and 0.1% when unknown sample solutions were prepared at 500 mg/10 mL. The standard curve was prepared from the concentration of the standard solution and the peak areas by operating under the aforementioned HPLC condition. Separately, 500 mg of an unknown sample was weighed accurately and water was added to make exactly 10 mL to prepare a sample solution. The amounts of D-glucose and D-mannose in the sample solution were calculated by measuring the concentrations from the areas of peaks corresponding to the elution location of D-glucose and D-mannose based on the standard curve.

Example 1

Various samples of sugars and sugar alcohols were mixed with oseltamivir phosphate and the color development was confirmed by the following method. Nine parts by weight of a test sample and one part by weight of oseltamivir phosphate were mixed in a mortar, and the mixture was transferred to a No. 1 standard brown glass bottle (volume: 14 ml) and the bottle was tightly sealed by a polyethylene middle stopper and a polypropylene screw cap. The color of the mixture immediately after mixing was measured by a color difference meter. The mixture was kept in the following two conditions: i) 2 weeks in a 60° C. incubator, or ii) one month in a 40° C. incubator at 75% RH while the bottle was open. Thereafter, the color of the mixture was measured. The color difference before and after the storage ΔE*(CIE L*a*b*) was measured. The measurement of color difference was carried out according to JIS Z-8722, based on 0-45° rear spectrophotometric method using a spectrophotometric color difference meter (SE-2000) (Nippon Denshoku Ltd.).

The results are shown in Table 2. The A, B and C rank in the table represents ΔE*≤2.5, 2.5<ΔE*≤5.0 and ΔE*>5.0, respectively.

TABLE 2

Coloring by mixing with sugars and sugar alcohols

| Sample name | 60° C. for 2 weeks (sealed) | 40° C., 75% RH, one month (open) |
|---|---|---|
| Xylitol | B | C |
| Erythritol | A | B |
| D-sorbitol | C | C |
| Maltose | C | C |
| Reducing malt sugar molasses | C | B |
| Sucrose | A | B |
| D-Mannitol | A | A |
| Oseltamivir phosphate | A | A |

The equilibrium water content and the contents of glucose and mannose were measured in erythritol, D-sorbitol and D-mannitol among sugars and sugar alcohols used in Example 1, and the results are described below.

The equilibrium water content (25° C., relative humidity 70%) of erythritol was 0.1%, the glucose content was <0.001%, the mannose content was 0.001%. The equilibrium water content (25° C., relative humidity 70%) of D-sorbitol was 1.7%, the glucose content was 0.006%, and the mannose content was 0.032%. The equilibrium water content (25° C., relative humidity 70%) of D-mannitol was 0.0%, the glucose content was ND, and the mannose content was ND (ND: below detection limit).

Above results indicated that the coloring was suppressed when sugars and sugar alcohols with equilibrium water content of 1% or less and containing glucose and mannose as impurities at 0.01% or less were used.

Example 2

Twenty seven grams of a sugar alcohol and 3 g of oseltamivir phosphate were mixed in a mortar, and then kneaded by adding 1 mL of water to carry out the wet granulation. The mixture was dried in a 50° C. constant temperature drying oven for 3 hr to reduce the water content of the formulation to 1% by weight or less. The formulation was kept at 60° C. for 4 weeks under a tight seal and the change of color before and after the storage was measured by a color difference meter.

Results indicated that even if the water content in the formulation was less than 1% by weight, the coloring occurred when the contents of glucose and mannose were not 0.01% or less. Results are shown in Table 3.

TABLE 3

Amount of reducing sugar and color change

| Granulation medium | Additive | Glucose | Mannose | Color difference ΔE* |
|---|---|---|---|---|
| Water | D-mannitol | ND | ND | 3.4 |
|  | Erythritol | <0.001 | 0.001 | 4.7 |
|  | D-sorbitol 1 | 0.028 | ND* | 14.6 |
|  | D-sorbitol 2 | 0.006 | 0.032 | 11.2 |

*ND: below detection limit

These results reveal that when the content of either the reducing sugar, glucose or mannose was 0.02% by weight or above, a significant color development was observed. Thus the content of each reducing sugar must be kept below 0.01% by weight to suppress the color change.

Examples 3 to 6

Test production of 1-kg scale was carried out, and granulation of the granule containing 1 to 10% of oseltamivir phosphate as a major active ingredient was investigated. Raw materials were weighed according to the following composition rates, and placed in a high speed mixing granulator. After mixing, wet granulation was carried out while adding water, and then the products were dried by a fluid bed dryer after wet granulation and subjected to dry-sorting to obtain granules.

TABLE 4

Composition ratios of oseltamivir phosphate/erythritol (% by weight)

| Component | Example 3 | Example 4 | Example 5 | Example 6 |
|---|---|---|---|---|
| Oseltamivir phosphate | 1.31 | 3.94 | 6.57 | 13.14 |
| Erythritol* | 87.69 | 85.06 | 82.43 | 75.86 |
| Povidone | 5 | 5 | 5 | 5 |
| Starch partially converted to pregelatinized starch | 5 | 5 | 5 | 5 |
| Acesulfame potassium | 0.5 | 0.5 | 0.5 | 0.5 |
| Stevia extracts | 0.5 | 0.5 | 0.5 | 0.5 |
| Total | 100 | 100 | 100 | 100 |

*Equilibrium water content (25° C., relative humidity 70%) is 0.1%, the contents of glucose and mannose as impurities are <0.001% and 0.001%, respectively.

These granules were transferred to No. 4 standard brown glass bottles (volume: 37.5 ml) and the bottles were tightly sealed by a polyethylene middle stopper and a polypropylene screw cap. The samples prepared according such a procedure were stored at 60° C. for 2 weeks and at 40° C. for 3 months, and then a residual rate of oseltamivir phosphate and color difference were measured. Results obtained are shown in Table 5.

TABLE 5

Residual rate (% by weight) and color difference of oseltamivir phosphate

| | Example 3 | Example 4 | Example 5 | Example 6 |
|---|---|---|---|---|
| Oseltamivir phosphate content (%) | 1.31 | 3.94 | 6.57 | 13.14 |
| at 60° C. for 2 weeks, residual rate (%) | 97 | 98 | 99 | 100 |

TABLE 5-continued

Residual rate (% by weight) and color difference of oseltamivir phosphate

|  | Example 3 | Example 4 | Example 5 | Example 6 |
|---|---|---|---|---|
| at 40° C. for 3 months, residual rate (%) | 99 | 99 | 99 | 100 |
| at 60° C. for 2 weeks, color difference (ΔE*) | 6.0 | 5.3 | 5.0 | 4.3 |
| at 40° C. for 3 months, color difference (ΔE*) | 2.9 | 3.8 | 3.0 | 2.6 |

Results of the 60° C. storage test indicated that the higher the content of the main active ingredient was, the better was the preservation stability against heat. Further, the results of the 40° C. storage test indicated that any of the compositions possesses sufficient stability as pharmaceutical compositions.

Examples 7 and 8

To prevent aggregation of manufactured granules among themselves, 0.05% or 0.1% of light anhydrous silicic acid was added to the granules produced according to Example 4 and mixed for 10 min in a V-type mixer, and then place in tightly sealed glass bottles with a drying agent. The bottles were stored at 40° C. for 3 months, and aggregation of granules was evaluated before and after the storage. Results are shown in Table 6.

TABLE 6

|  | Amount of light anhydrous silicic acid (%) | Condition after | |
|---|---|---|---|
|  |  | Before storage | 3 months at 40° C. |
| Example 4 | 0 | No aggregation | Light aggregation |
| Example 7 | 0.05 | No aggregation | No aggregation |
| Example 8 | 0.1 | No aggregation | No aggregation |

Slight degree of aggregation was observed in the composition of Example 4 (the aggregates were easily disintegrated by turning the bottle upside-down) but aggregation was completely prevented by adding light anhydrous silicic acid.

Examples 9 to 13

The pharmaceutical composition was produced at 25-kg scale by the following composition ratio. After Components I were placed in a high speed mixing granulator and mixed, the wet granulation was carried out by spraying binding water, and the products were dried by a fluid bed dryer and subjected to dry-sorting to obtain granules. Components II were added to the granules and mixed in a V-type mixer. The results are shown in Table 7.

TABLE 7

| Component | | Example 9 | Example 10 | Example 11 | Example 12 | Example 13 |
|---|---|---|---|---|---|---|
| Oseltamivir phosphate | I | 3.94 | 3.94 | 3.94 | 3.94 | 3.94 |
| Erythritol* | I | — | 85.06 | 83.46 | 85.26 | 87.26 |
| D-mannitol** | I | 85.06 | — | — | — | — |
| Povidone | I | 5 | 5 | 5 | 5 | 3 |
| Cornstarch | I | 5 | 5 | 5 | 5 | 5 |
| Dipotassium glycyrrhizate | I | 1 | 1 | 1 | — | — |
| Acesulfame potassium | I | — | — | 1 | 0.1 | 0.1 |
| Saccharin sodium | I | — | — | — | 0.1 | 0.1 |
| Light anhydrous silicic acid | II | — | — | 0.1 | 0.1 | 0.1 |
| Flavor | II | — | — | 0.5 | 0.5 | 0.5 |
| Total | | 100 | 100 | 100 | 100 | 100 |
| Result of stability test | Color difference ΔE* (at 60° C. for 2 weeks) | 2.85 | 4.74 | 6.56 | 2.71 | 1.92 |
| | Color difference ΔE* (at 40° C. for 3 months) | — | — | — | 2.20 | 1.52 |
| | Residual rate at 60° C. for 2 weeks (%) | 97.37 | 97.14 | 97.25 | 102.33 | 99.02 |

*Equilibrium water content (25° C., relative humidity 70%) is 0.1%, the contents of glucose and mannose as impurities are <0.001% and 0.001%, respectively.
**Equilibrium water content (25° C., relative humidity 70%) is 0.0%, the contents of glucose and mannose as impurities are ND and ND (ND: below detection limit), respectively.

The results of the storage tests in the conditions at 60° C. for 2 weeks and at 40° C. for 3 months indicates that each of the compositions has sufficient stability as pharmaceutical compositions.

INDUSTRIAL APPLICABILITY

The present invention provides a pharmaceutical composition containing oseltamivir phosphate that has an improved preservation stability, in particular, the preservation stability against temperature and humidity in the storage environment, and further in which coloring during the storage is prevented.

The invention claimed is:
1. A pharmaceutical composition, comprising:
one or more excipients selected from sugars and sugar alcohols in which the sugar or sugar alcohol is selected from erythritol, D-mannitol, sucrose or a mixture thereof; and
oseltamivir phosphate,
wherein an amount of each of glucose and mannose contained in the sugars and sugar alcohols as impurities is 0.01% by weight or less, and
wherein the form of the pharmaceutical composition is in the form of a dry syrup.

2. The pharmaceutical composition according to claim 1, wherein the composition is used for treatment of influenza virus infection and conditions associated with the infection selected from bronchitis, pneumonia, generalized pain and fever.

3. The pharmaceutical composition according to claim 1, further comprising one or more water-soluble polymers selected from povidone, methylcellulose, carmellose sodium and macrogol 6000.

4. The pharmaceutical composition according to claim 1, further comprising one or more high-intensity sweeteners.

5. The pharmaceutical composition according to claim 4, wherein the high-intensity sweetener is selected from dipotassium glycyrrhizate, stevia extracts, acesulfame potassium and saccharin sodium.

6. The pharmaceutical composition according to claim 1, further comprising one or more anti-caking agents.

7. The pharmaceutical composition according to claim 6, wherein the anti-caking agent selected from light anhydrous silicic acid and cornstarch.

8. A method for treatment of influenza virus infection and conditions associated with the infection selected from bronchitis, pneumonia, generalized pain and fever, comprising administering to a patient in need thereof a pharmaceutical composition comprising:
one or more pharmaceutically acceptable excipients selected from sugars and sugar alcohols in which the sugar or sugar alcohol is selected from erythritol, D-mannitol and sucrose or a mixture thereof; and
an effective amount of oseltamivir phosphate,
wherein an amount of each of glucose and mannose contained in the sugars and sugar alcohols as impurities is 0.01% by weight or less, and
wherein the form of the pharmaceutical composition is in the form of a dry syrup.

* * * * *